US012350421B1

(12) United States Patent
Zhang et al.

(10) Patent No.: US 12,350,421 B1
(45) Date of Patent: Jul. 8, 2025

(54) LOADING ASSEMBLY FOR INHALER AND INHALER

(71) Applicant: SUZHOU SINGMED MEDICAL DEVICE SCIENCE AND TECHNOLOGY LTD., Suzhou (CN)

(72) Inventors: Fei Zhang, Jiangsu Province (CN); Xiaoyuan Sun, Jiangsu Province (CN); Guangtao Zhao, JIANGSU PROVINCE (CN)

(73) Assignee: SUZHOU SINGMED MEDICAL DEVICE SCIENCE AND TECHNOLOGY LTD., Jiangsu Province (CN)

( * ) Notice: Subject to any disclaimer, the term of this patent is extended or adjusted under 35 U.S.C. 154(b) by 0 days.

(21) Appl. No.: 19/037,898

(22) Filed: Jan. 27, 2025

Related U.S. Application Data

(63) Continuation of application No. PCT/CN2024/126163, filed on Oct. 21, 2024.

(30) Foreign Application Priority Data

Jul. 3, 2024 (CN) .......................... 202410885061.4

(51) Int. Cl.
*A61M 11/02* (2006.01)
*A61M 15/00* (2006.01)

(52) U.S. Cl.
CPC .......... *A61M 11/02* (2013.01); *A61M 15/009* (2013.01); *A61M 2202/0468* (2013.01)

(58) Field of Classification Search
CPC ................ A61M 11/02; A61M 15/009; A61M 2202/0468; B05B 17/00–085
See application file for complete search history.

(56) References Cited

U.S. PATENT DOCUMENTS

| 2015/0040893 | A1* | 2/2015 | Besseler | ........... A61M 15/0071 128/200.21 |
| 2021/0252234 | A1* | 8/2021 | Bartels | .................. B05B 11/109 |

FOREIGN PATENT DOCUMENTS

| CN | 112423895 A | 2/2021 |
| CN | 114007674 A | 2/2022 |
| CN | 116829218 A | 9/2023 |
| CN | 117427246 A | 1/2024 |
| CN | 117548251 A | 2/2024 |

(Continued)

*Primary Examiner* — Elliot S Ruddie
(74) *Attorney, Agent, or Firm* — FisherBroyles, LLP; John K. Shimmick

(57) ABSTRACT

A loading assembly for an inhaler and an inhaler is provided. The loading assembly includes: an actuator; a first component including a first helical end surface; and a second component including: a helical section having a second helical end surface for mating with the first helical end surface; and a horizontal section adjacent to the helical section. The first component and the second component are configured such that the second component is capable of moving away from the first component to a preloaded position in the case where the second component rotates relative to the first component in a first direction along the mating first and second helical end surfaces, and the actuator is configured to carry the horizontal section to block the second component from leaving the preloaded position in the case where the second component has been moved to the preloaded position.

18 Claims, 8 Drawing Sheets

(56) References Cited

FOREIGN PATENT DOCUMENTS

| | | |
|---|---|---|
| CN | 117838997 A | 4/2024 |
| CN | 221243662 U | 7/2024 |
| EP | 2633919 A2 | 9/2013 |

\* cited by examiner

LOADING ASSEMBLY FOR INHALER AND INHALER

CROSS REFERENCE TO RELATED APPLICATIONS

The present application is a continuation of the international application PCT/CN2024/126163, filed on Oct. 21, 2024 and entitled "LOADING ASSEMBLY FOR INHALER AND INHALER", and the international application claims the right of priority of the Chinese patent application No. 202410885061.4 filed on Jul. 3, 2024 and entitled "TRIGGER ASSEMBLY FOR INHALER, AND INHALER", which is incorporated herein by reference in its entirety.

TECHNICAL FIELD

The disclosure relates to the technical field of atomization, and in particular to a loading assembly for an inhaler, and an inhaler.

BACKGROUND

Inhalers can atomize a liquid (e.g., a medical liquid) into droplets. In the related art, a container in an inhaler contains a liquid to be atomized or sprayed, and during the movement of the container relative to a spraying assembly, the liquid in the container can be atomized, and the atomized liquid can be sprayed out of a spray nozzle of the spraying assembly.

SUMMARY OF THE INVENTION

The disclosure provides a loading assembly for an inhaler, and an inhaler.

According to an aspect of the disclosure, there is provided a loading assembly for an inhaler, the loading assembly including: an actuator; a first component including a first helical end surface; and a second component including: a helical section having a second helical end surface for mating with the first helical end surface; and a horizontal section adjacent to the helical section. The first component and the second component are configured such that the second component is capable of moving away from the first component to a preloaded position in the case where the second component rotates relative to the first component in a first direction along the mating first and second helical end surfaces, and the actuator is configured to carry the horizontal section to block the second component from leaving the preloaded position in the case where the second component has been moved to the preloaded position.

According to another aspect of the disclosure, there is provided an inhaler, the inhaler including a liquid reservoir and a loading assembly configured to load liquid from the liquid reservoir into a pumping chamber of the inhaler, the loading assembly including: an actuator; a first component including a first helical end surface; and a second component including: a helical section having a second helical end surface for mating with the first helical end surface; and a horizontal section adjacent to the helical section. The first component and the second component are configured such that the second component is capable of moving away from the first component to a preloaded position in the case where the second component rotates relative to the first component in a first direction along the mating first and second helical end surfaces, and the actuator is configured to carry the horizontal section to block the second component from leaving the preloaded position in the case where the second component has been moved to the preloaded position.

BRIEF DESCRIPTION OF THE DRAWINGS

More details, features, and advantages of the disclosure are disclosed in the following description of exemplary embodiments with reference to the accompanying drawings, in which.

DETAILED DESCRIPTION

In the disclosure, unless otherwise stated, the terms "first", "second", etc., used to describe various elements are not intended to limit the positional, temporal or importance relationship of these elements, but rather only to distinguish one component from another. In some examples, a first element and a second element may refer to a same instance of the element, and in some cases, based on contextual descriptions, the first element and the second element may also refer to different instances.

In the scope of the present disclosure, a "inhaler" refers to an apparatus for atomizing a liquid. Typically, the inhaler is configured to atomize a fluid (e.g., a liquid drug or similar fluid) and spray the atomized fluid to the mouth or nose of a user (e.g., a patient).

The disclosure provides a loading assembly for an inhaler, and an inhaler. Within the scope of the disclosure, the loading assembly may be mounted in the inhaler and may be in linkage with a push switch/or a rotary switch of the inhaler. The loading assembly provided in the disclosure includes an actuator; a first component including a first helical end surface; and a second component including: a helical section having a second helical end surface for mating with the first helical end surface; and a horizontal section adjacent to the helical section. The first component and the second component are configured such that the second component is capable of moving away from the first component to a preloaded position in the case where the second component rotates relative to the first component in a first direction along the mating first and second helical end surfaces, and the actuator is configured to carry the horizontal section to block the second component from leaving the preloaded position in the case where the second component has been moved to the preloaded position. The helical section of the second component has the second helical end surface for mating with the first helical end surface, so that the second component is capable of moving away from the first component to the preloaded position during relative rotation between the second component and the first component along the mating first and second helical end surfaces, thus achieving smooth liquid loading. Moreover, since the second component has the horizontal section adjacent to the helical section, the horizontal section of the second component can be stably carried on the actuator after a smooth transition from a loading process to a position where loading is completed (i.e., the preloaded position), thus preventing undesired disengagement of the second component from the actuator, and avoiding accidental spraying.

Figure 1:
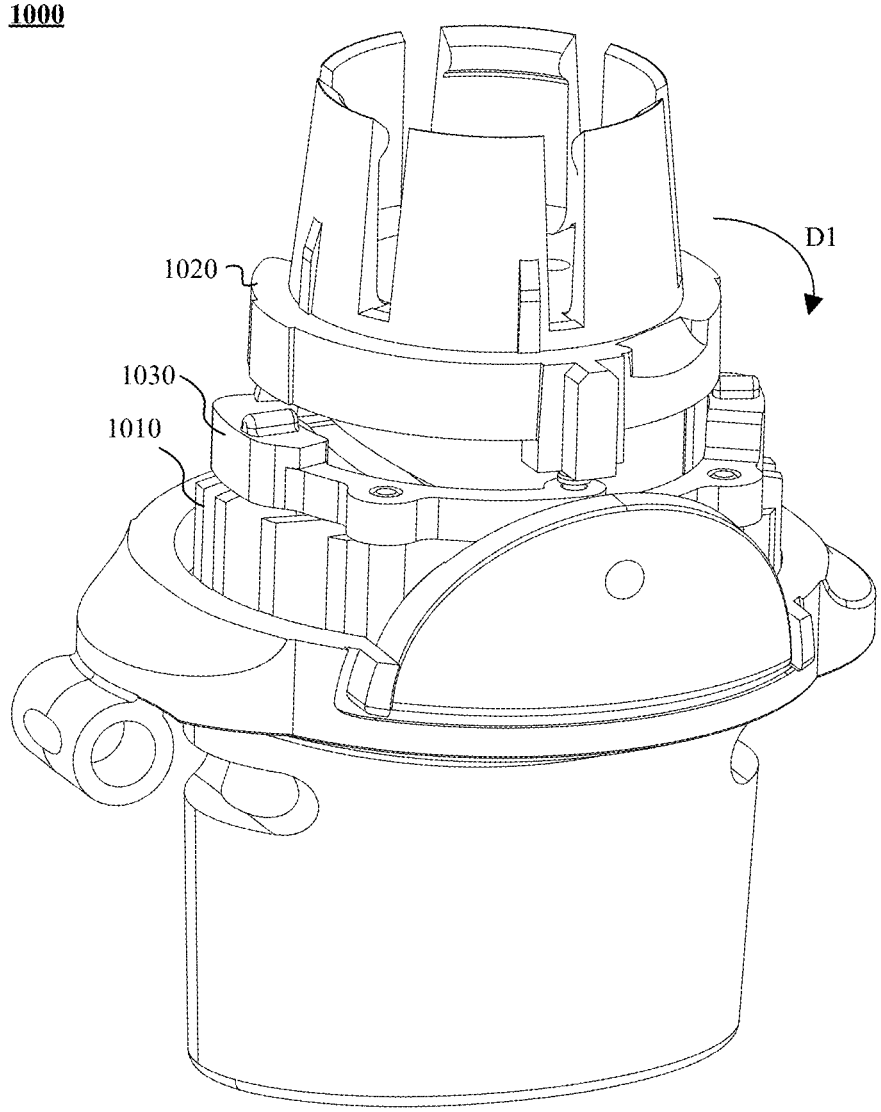
FIG. 1 is a schematic diagram illustrating a loading assembly for an inhaler in a triggered position state according to an exemplary embodiment.
Figure 2:
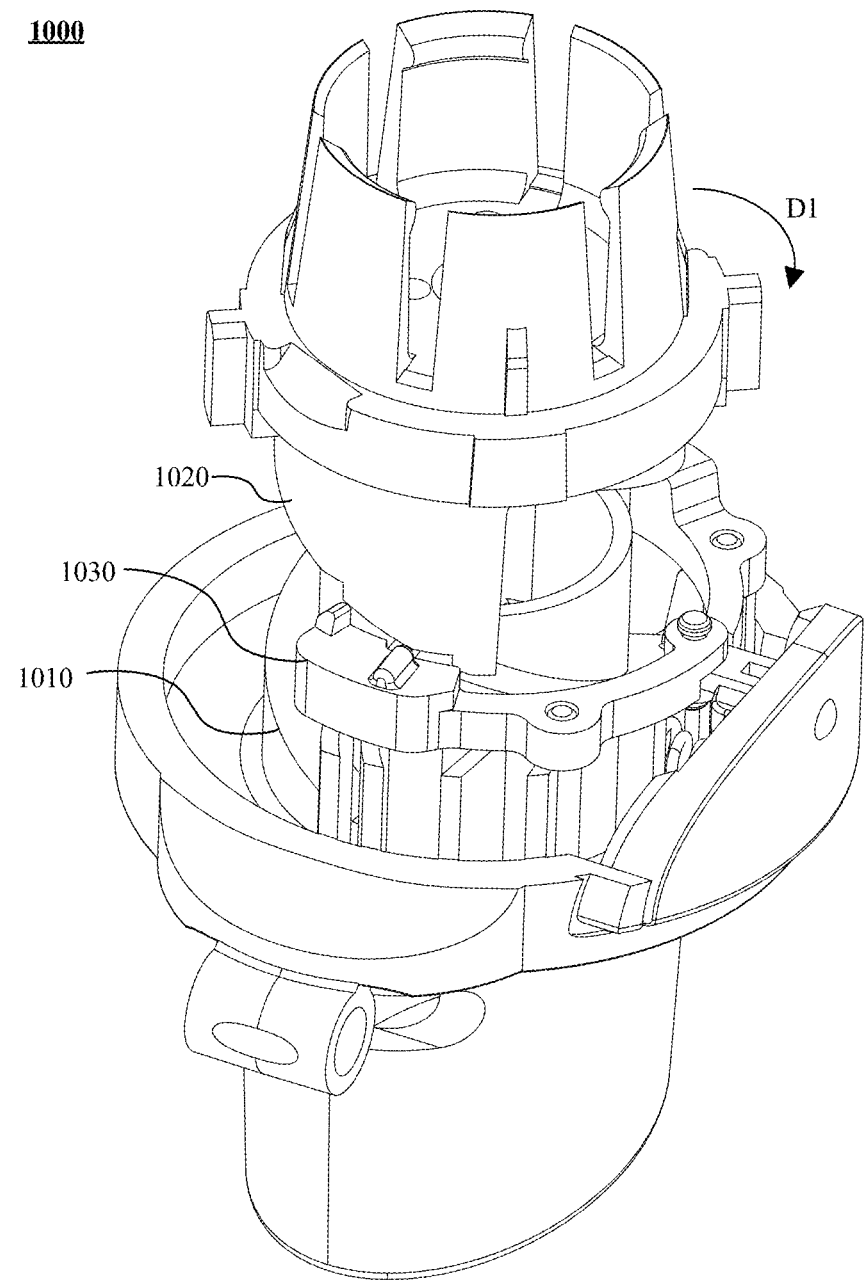
FIG. 2 is a schematic diagram illustrating the loading assembly for an inhaler in an intermediate state according to an exemplary embodiment.
Figure 3:
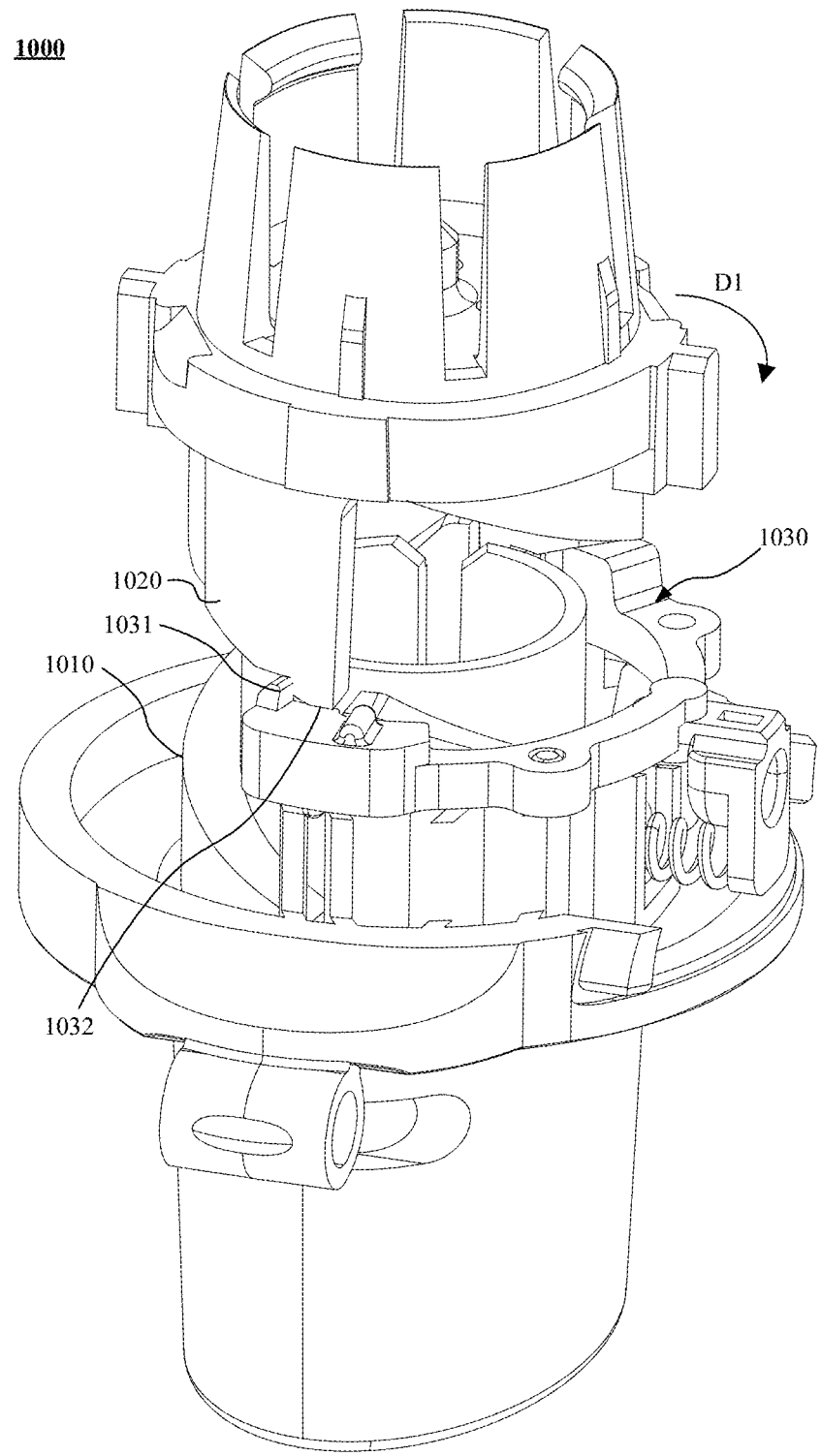
FIG. 3 is a schematic diagram illustrating the loading assembly for an inhaler in a preloaded position state according to an exemplary embodiment.
Figure 4:
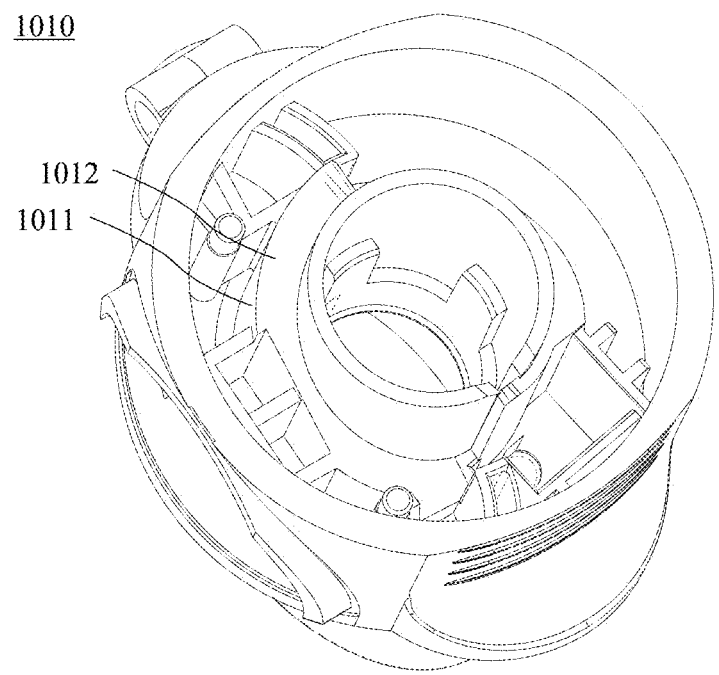
FIG. 4 is a schematic diagram illustrating a first component of the loading assembly for an inhaler according to an exemplary embodiment.
Figure 5:
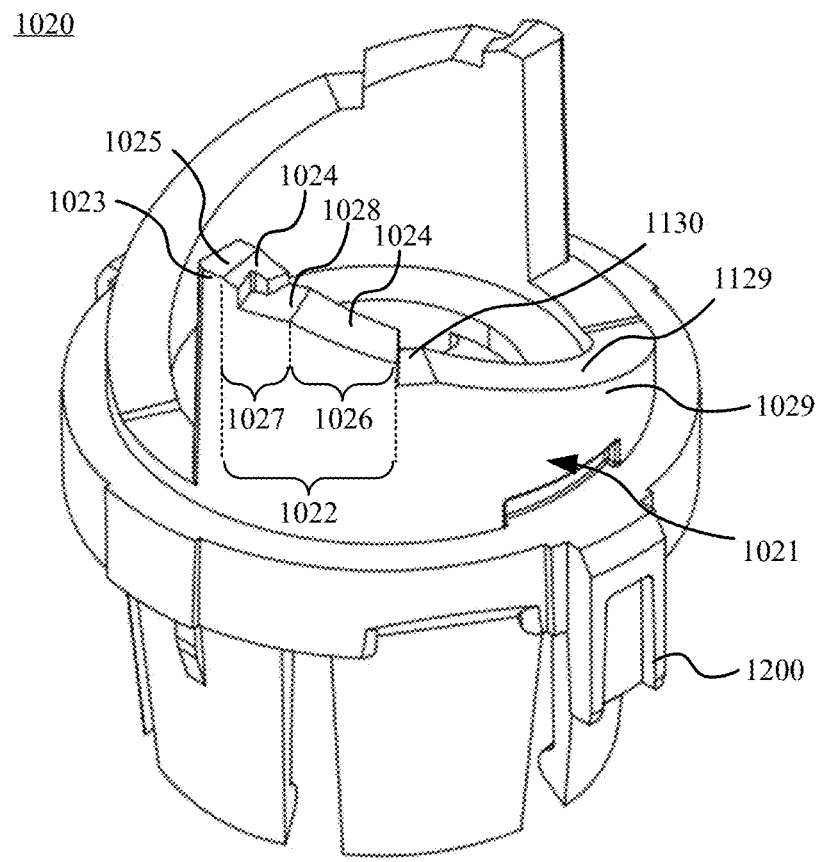
FIG. 5 is a schematic diagram illustrating a second component of the loading assembly for an inhaler according to an exemplary embodiment.
Figure 6:
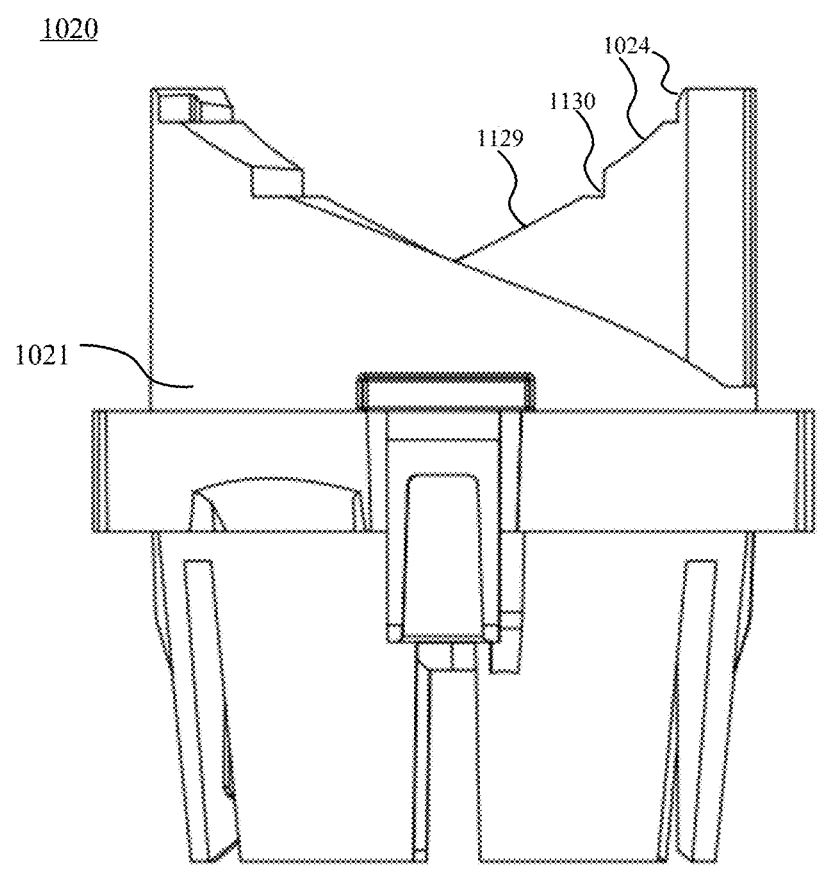
FIG. 6 is another schematic diagram illustrating the second component of the loading assembly for an inhaler according to an exemplary embodiment.

The loading assembly according to an exemplary embodiment will be described below with reference to FIGS. 1 to 6. FIG. 1 is a schematic diagram illustrating a loading assembly for an inhaler in a triggered position state according to an exemplary embodiment; FIG. 2 is a schematic diagram illustrating the loading assembly for an inhaler in an intermediate state according to an exemplary embodiment; and FIG. 3 is a schematic diagram illustrating the loading assembly for an inhaler in a preloaded position state according to an exemplary embodiment. Furthermore, FIG. 4 is a schematic diagram illustrating a first component of the loading assembly for an inhaler according to an exemplary embodiment; and FIG. 5 and FIG. 6 are schematic diagrams illustrating a second component of the loading assembly for an inhaler according to an exemplary embodiment.

In the scope of the present disclosure, the "preloaded position" of the loading assembly may refer to a position where a liquid in the inhaler is loaded to be prepared for outward spraying (e.g., from a reservoir into a pumping chamber). In this position, if there is no triggering action of an external force, the inhaler cannot spray, and only by triggering the loading assembly, for example, by manually operating (e.g., pressing), the loading assembly can be restored from the "preloaded position" to the "triggered position", i.e., the liquid in the inhaler is switched from a state in which the liquid is already loaded for pre-spraying, to a state of spraying. In the "triggered position", the inhaler can be operated (e.g., rotated) again to the "preloaded position", and therefore the "triggered position" may also be referred to as an initial position.

Firstly, with reference to FIGS. 1 to 3, a loading assembly 1000 for an inhaler includes: a first component 1010, a second component 1020, and an actuator 1030.

The second component 1020 in FIG. 1 is in the triggered position (i.e., the initial position), the second component 1020 in FIG. 3 is in the preloaded position, and the second component 1020 in FIG. 2 is in an intermediate state between the triggered position and the preloaded position. In an example, in the preloaded position, liquid drug may be pumped from a reservoir into a pumping chamber arranged at the first component 1010 or the second component 1020; and In case of a transition from the preloaded position to the triggered position, the liquid drug can be sprayed from the pumping chamber outwards through a nozzle, and accordingly, after the spraying is completed, the second component 1020 in the triggered position is in an initial position of the next cycle of action and can thus move to the preloaded position again.

Referring to FIG. 4, the first component 1010 includes a first mating portion 1011. The first mating portion 1011 has a first helical end surface 1012. As seen in FIG. 4, the first mating portion 1011 may extend helically upwardly from a bottom position to a top position of a body of the first component 1010, and correspondingly, the first mating portion 1011 extending helically forms the first helical end surface 1012.

Referring to FIGS. 5 and 6, the second component 1020 includes a second mating portion 1021. The second mating portion 1021 includes a helical section 1022 and a horizontal section 1023. The helical section 1022 has a second helical end surface 1024 for mating with the first helical end surface 1012 of the first mating portion 1011. The horizontal section 1023 is adjacent to the helical section 1022.

The first component 1010 and the second component 1020 are configured such that the second component is capable of moving away from the first component 1010 to the preloaded position in the case where the second component 1020 rotates relative to the first component 1010 in a first direction D1 along the first helical end surface 1012 and the second helical end surface 1024 that mate with each other. For example, referring to FIGS. 1 to 3, starting from the position shown in FIG. 1, the second component 1020 rotates relative to the first component 1010 in a clockwise direction in FIG. 1, and as shown in FIG. 2, as the second component 1020 rotates, the second component 1020 gradually moves away from the first component 1010; and as the second component 1020 further rotates in the clockwise direction, the second component 1020 moves to the preloaded position as shown in FIG. 3. It will be appreciated that the process of the second component 1020 moving away from the first component 1010 to the preloaded position may refer to that the first component 1010 is fixed while the second component 1020 moves; or that the second component 1020 is fixed while the first component 1010 moves.

The actuator 1030 is configured to carry the horizontal section 1023 (e.g., a horizontal end surface 1025 of the horizontal section 1023) to block the second component 1020 from leaving the preloaded position in the case where the second component 1020 has been moved to the preloaded position.

The helical section 1022 of the second component 1020 has the second helical end surface 1024 for mating with the first helical end surface 1012, so that the second component 1020 is capable of moving away from the first component 1010 to the preloaded position during relative rotation between the second component 1020 and the first component 1010 along the first helical end surface 1012 and the second helical end surface 1024 that mate with each other, thus achieving a smooth liquid loading. Moreover, since the second component 1020 has the horizontal section 1023 adjacent to the helical section 1022, the second component 1020 can be stably carried on the actuator 1030 after a smooth transition from a loading process to a position where loading is completed (i.e., the preloaded position), thus preventing undesired disengagement of the second component 1020 from the actuator 1030, and avoiding accidental spraying.

In some embodiments, as shown in FIG. 3, the actuator 1030 may include a limiting protrusion 1031. The limiting protrusion 1031 is configured to block the second component 1020 in the preloaded position from rotating in the first direction D1. As shown in FIG. 5, the helical section 1022 includes a first sub-section 1026 and a second sub-section 1027 between the first sub-section 1026 and the horizontal section 1023. A recess 1028 for accommodating the limiting protrusion 1031 of the actuator 1030 is provided in the second sub-section 1027. Since the recess 1028 for accommodating the limiting protrusion 1031 of the actuator 1030 is further provided in the helical section 1022, undesired rotation between the second component 1020 and the first component 1010 in the first direction D1 can be prevented by means of a simple structure, and the limiting protrusion 1031 accommodated in the recess 1028 will not take up additional space; and such a configuration also does not affect the horizontal section 1023 and accordingly does not affect the stable carrying effect of the actuator 1030 on the second component 1020.

In some embodiments, with continued reference to FIG. 5, the recess 1028 in the second sub-section 1027 is recessed downwardly from the second helical end surface 1024 of the second sub-section 1027. For example, the recess 1028 may be formed by removing material from (e.g., by machining, by laser machining, or by etching) the complete second helical end surface 1024 of the second sub-section 1027. Therefore, not only is the processing of the recess 1028 convenient, but the shape of the recess 1028 can be flexibly adjusted according to the shape of the protrusion 1031.

In some embodiments, as shown in FIGS. 5 and 6, the second helical end surface 1024 of the second sub-section 1027 is in the same helical surface as the second helical end surface 1024 of the first sub-section 1026. Therefore, even with the presence of the recess 1028, when the second component 1020 rotates relative to the first component 1010 in the first direction D1 along the first helical end surface 1012 and the second helical end surface 1024 that mate with each other, since the second helical end surface 1024 of the second sub-section 1027 is in the same helical surface as the second helical end surface 1024 of the first sub-section 1026, the rotation process can still be carried out smoothly without bumping or jamming, further improving the user experience.

In some embodiments, with continued reference to FIGS. 3 and 5, the actuator 1030 may be partially arranged around at least one of the first component 1010 or the second component 1020, the actuator 1030 may include a bearing surface 1032 for carrying the horizontal section 1023, and the limiting protrusion 1031 is arranged on a radial inner side of the bearing surface 1032. Moreover, the recess 1028 in the second sub-section 1027 is arranged on a radial outer side of the second component 1020. For example, the actuator 1030 may be connected to the first component 1010 and partially arranged around an outer periphery of the first mating portion 1011. Alternatively, the actuator 1030 may be connected to the second component 1020 and partially arranged around an outer periphery of the second mating portion 1021. Alternatively, the actuator 1030 may be connected to both the first component 1010 and the second component 1020 and partially arranged around both the first mating portion 1011 and the second mating portion 1021. For example, a main body of the actuator 1030 may have a substantially annular shape, such that an inner periphery of the actuator can substantially surround the first component 1010 or the second component 1020 having a substantially cylindrical outer surface. Since the limiting protrusion 1031 is arranged on the radial inner side of the bearing surface 1032 and the recess 1028 in the second sub-section 1027 is arranged on the radial outer side of the second component 1020, the limiting protrusion 1031 arranged around the first component 1010 or the second component 1020 can smoothly enter the recess 1028 of the second sub-section 1027, thus reducing jamming.

In some embodiments, the actuator 1030 may be configured in the shape of a curved arm arranged around at least one of the first component 1010 or the second component 1020. The curved arm may be configured such that when the bearing surface 1032 of the curved arm is in contact with the horizontal section 1023 of the second component 1020, the limiting protrusion 1031 of the curved arm enters the recess 1028 in the second sub-section 1027. In an example, a pair of second components 1020 in rotational symmetry may be provided, and right and left curved arms may be provided accordingly, making the loading process more stable.

In some embodiments, with continued reference to FIG. 5, the horizontal section 1023 has a horizontal end surface 1025, and the second helical end surface 1024 of the second sub-section 1027 is in a smooth transition with the horizontal end surface 1025 of the horizontal section 1023. In this way, when the first helical end surface 1012 slides along the second helical end surface 1024 of the second sub-section 1027, a smooth transition to the horizontal end surface 1025 of the horizontal section 1023 is enabled, thus further reducing jamming. In an example, there may be a chamfer between the second helical end surface 1024 of the second sub-section 1027 and the horizontal end surface 1025 of the horizontal section 1023.

In some embodiments, a bottom surface of the recess 1028 of the second sub-section 1027 is in a smooth transition with the second helical end surface 1024 of the first sub-section 1026. In this way, the limiting protrusion 1031 of the actuator 1030 can enter the recess 1028 more smoothly, thus reducing jamming. In an example, there may be a chamfer between the bottom surface of the recess 1028 of the second sub-section 1027 and the second helical end surface 1024 of the first sub-section 1026.

In some embodiments, the recess 1028 of the second sub-section 1027 may make the second helical end surface 1024 of the second sub-section 1027 discontinuous from the second helical end surface 1024 of the first sub-section 1026. As shown in FIG. 5, the second helical end surface 1024 may be discontinuous at at least a portion of the helical section 1022, which allows for providing, in the limited space of the second mating portion 1021 of the second component 1020, the recess 1028 large enough to accommodate the limiting protrusion 1031 of the actuator 1030, without affecting the smooth sliding of the first helical end surface 1012 on the second helical end surface 1024. For example, at the same time, the first helical end surface 1012 slides on at least one of the second helical end surface 1024 of the second sub-section 1027 and the second helical end surface 1024 of the first sub-section 1026.

In some embodiments, as shown in FIG. 5, the second component 1020 includes a second mating portion 1021, the helical section 1022 and the horizontal section 1023 are arranged on the second mating portion 1021, and the horizontal section 1023 has a horizontal end surface 1025. In the second mating portion 1021, the horizontal end surface 1025 is furthest away from a body of the second component 1020, and a distance of the second helical end surface 1024 of the helical section 1022 from the body of the second component 1020 gradually decreases as the helical section 1022 extends away from the horizontal section 1023.

In some embodiments, with continued reference to FIG. 5, the second component 1020 may further include a reinforced section 1029. The reinforced section 1029 extends from the body of the second component 1020 and is connected to the helical section 1022. In this way, by providing the reinforced section 1029 connected to the helical section 1022, the structural strength of the helical section 1022 can be reinforced, such that the second component 1020, especially the second mating portion 1021 of the second component 1020, is more stable as a whole.

In some embodiments, with continued reference to FIGS. 5 and 6, the reinforced section 1029 may have a third helical end surface 1129, and a step 1130 is provided between the third helical end surface 1129 and the second helical end surface 1024 of the helical section 1022 such that the first helical end surface 1012 is not in contact with the third helical end surface 1129 if the first helical end surface 1012 mates with the second helical end surface 1024. For example, the helical surface where the third helical end surface 1129 is located may be generally lower than the helical surface where the second helical end surface 1024 is located. In this way, the reinforced section 1029 has a structure reinforcing function, and the third helical end surface 1129 of the reinforced section 1029 will not contact the first helical end surface 1012 to produce unnecessary frictional resistance, thus ensuring a smoother loading process.

In some embodiments, the loading assembly 1000 may further include an elastic member (not shown). The elastic member is configured to store energy when the second component 1020 moves away from the first component 1010; and the actuator 1030 may be configured to, upon being triggered, release the second component 1020 such that the second component 1020 moves toward the first component 1010 to the triggered position under the action of the elastic member. In an example, the elastic member may include a spring or other elastic members, as long as energy can be stored by means of elastic deformation. In an example, the elastic member (e.g., the spring) may be arranged on a side of the second component 1020 close to the first component 1010, when the second component 1020 moves away from the first component 1010, tensile deformation occurs to store energy, and when the elastic member restores, the second component 1020 can be pushed into the triggered position by means of a pull force. In addition, the elastic member (e.g., the spring) may be arranged on the side of the second component 1020 away from the first component 1010, and is subjected to compression deformation to store energy when the second component 1020 moves away from the first component 1010, and the second component 1020 can be pushed to the triggered position by means of a push force when the elastic member restores.

In some embodiments, as shown in FIG. 5, at least one positioning guide portion 1200 may be provided at a circumferential edge of the second component 1020. The positioning guide portion 1200 may be configured to position and guide the second component 1020 during the process of mounting the second component 1020 to another component.

According to a second aspect of the disclosure, there is provided an inhaler.

Figure 7:
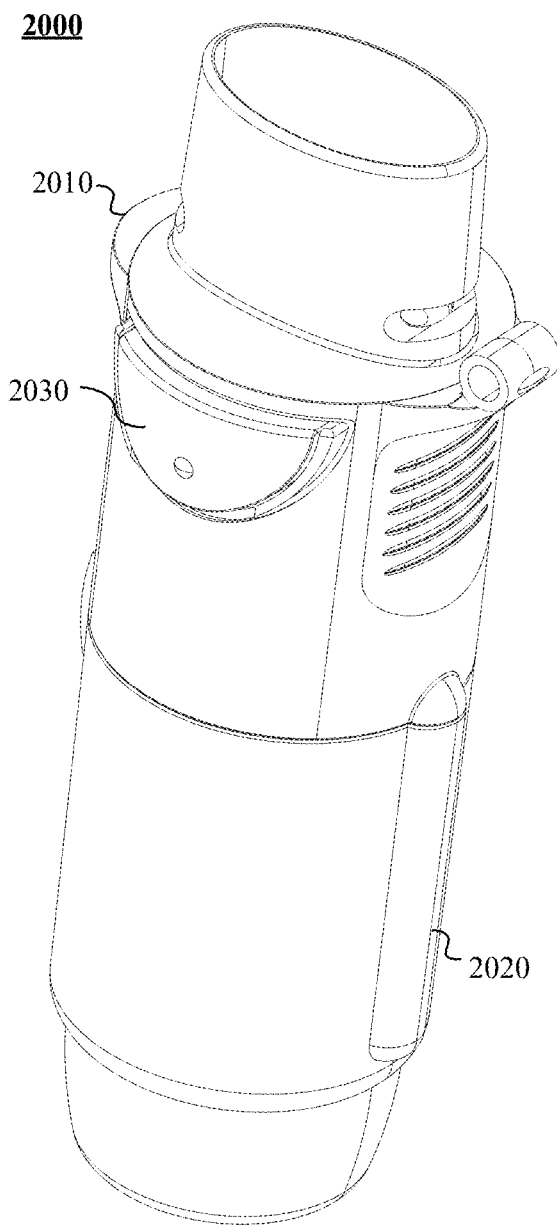
FIG. 7 is a perspective view illustrating an inhaler according to an exemplary embodiment.
Figure 8:
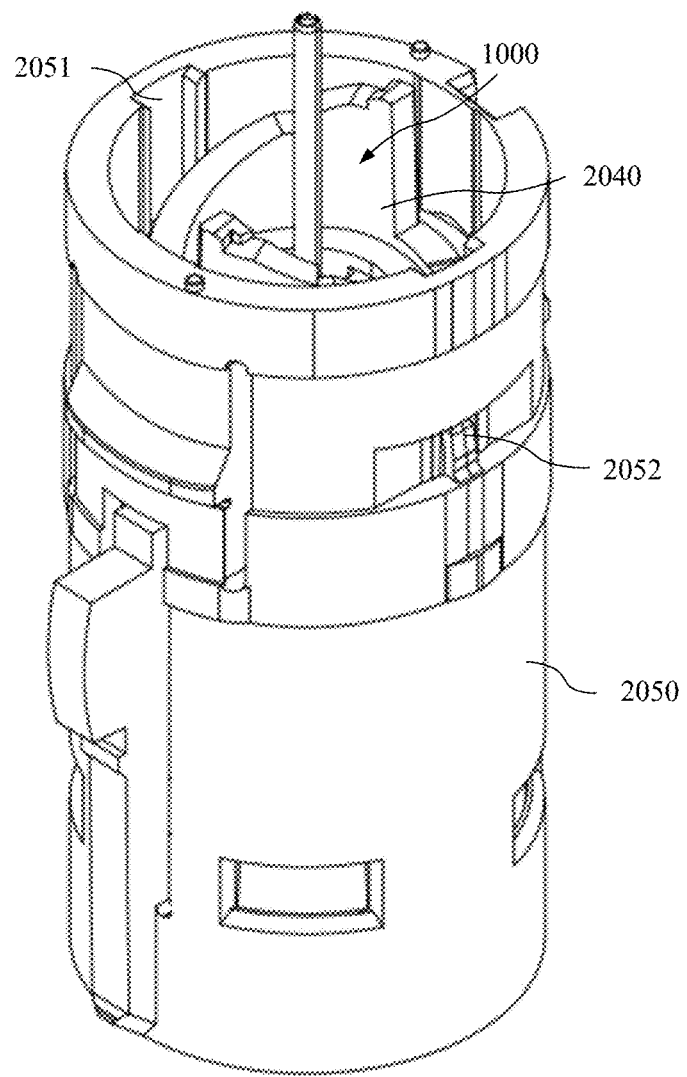
FIG. 8 is a perspective view illustrating the assembly of a delivery tube socket and a rotary housing of the inhaler according to an exemplary embodiment.
Figure 9:
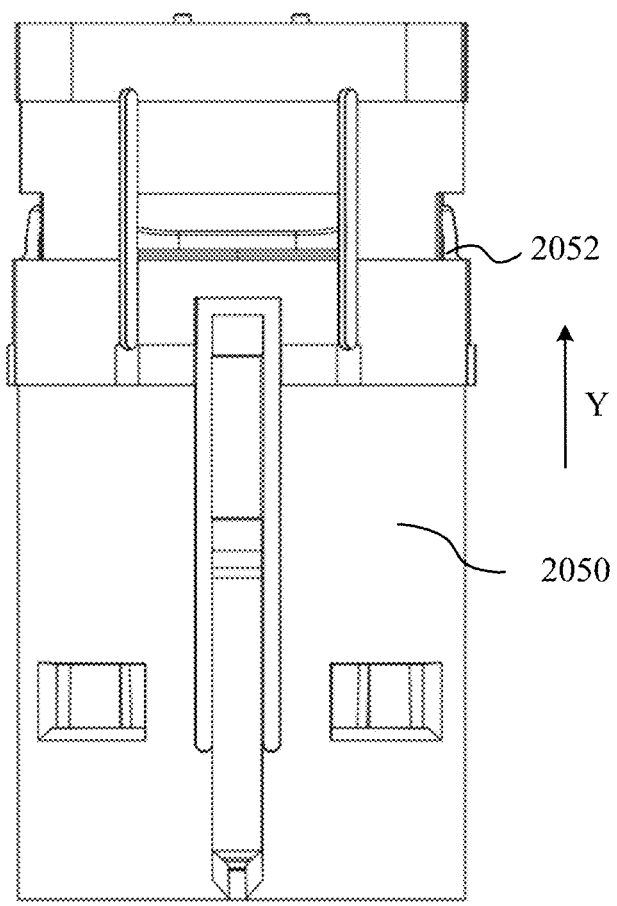
FIG. 9 is a perspective view illustrating the rotary housing of the inhaler according to an exemplary embodiment.

The inhaler of the disclosure is further described below with reference to FIGS. 7 to 9. FIG. 7 is a perspective view illustrating an inhaler according to an exemplary embodiment; FIG. 8 is a perspective view illustrating the assembly of a delivery tube socket and a rotary housing of the inhaler according to an exemplary embodiment; and FIG. 9 is a perspective view illustrating the rotary housing of the inhaler according to an exemplary embodiment.

As shown in FIG. 7, the inhaler 2000 may include an upper housing 2010, a lower housing 2020, a button 2030 arranged in the upper housing, and a liquid reservoir (not shown) arranged in the lower housing 2020.

Moreover, as shown in FIG. 8, the inhaler 2000 includes a loading assembly 1000. The loading assembly 1000 may be arranged inside the inhaler 2000 for loading liquid from the liquid reservoir into a pumping chamber of the inhaler 2000.

In some embodiments, a first component of the loading assembly 1000 may be configured as the upper housing 2010 of the inhaler 2000, and a second component of the loading assembly 1000 may be configured as a delivery tube socket 2040 of the inhaler 2000. In an example, the delivery tube socket 2040 may be configured to rotate along with rotation of the lower housing 2020 of the inhaler 2000. For example, the upper housing 2010 and the lower housing 2020 may rotate relative to each other, and the delivery tube socket 2040 may be indirectly coupled to the lower housing 2020. By rotating the lower housing 2020 relative to the upper housing 2010, the delivery tube socket 2040 can rotate relative to the upper housing 2010. In other words, by rotating the lower housing 2020 relative to the upper housing 2010, the second component 1020 of the loading assembly 1000 arranged in the inhaler 2000 can rotate relative to the first component 1010, and the second component 1020 moves away from the first component 1010 to the preloaded position. During this process, part of the liquid stored in the liquid reservoir of the inhaler 2000 may be pumped, for example, into the pumping chamber of the inhaler 2000 to for atomization and spraying.

In some embodiments, as shown in FIG. 8, the inhaler 2000 may further include a rotary housing 2050. The rotary housing 2050 is sleeved outside the delivery tube socket 2040, and an inner wall of the rotary housing 2050 may be provided with an axial slide groove 2051; and a positioning guide portion (e.g., the positioning guide portion 1200 shown in FIG. 5) capable of sliding in the axial slide groove 2051 is provided at a circumferential edge of the delivery tube socket 2040, and the positioning guide portion 1200 slides into the axial slide groove 2051 to restrict relative rotation between the delivery tube socket 2040 and the rotary housing 2050. In addition, the axial slide groove 2051 and the positioning guide portion 1200 can facilitate the mounting during assembly.

In an example, the rotary housing 2050 may be located inside the lower housing 2020 and arranged outside the delivery tube socket 2040. The rotary housing 2050 may transfer the rotation of the lower housing 2020 to the delivery tube socket 2040. In other words, the delivery tube socket 2040 rotates along with the rotation of the rotary housing 2050. In addition, when the delivery tube socket 2040 is released and moves toward the upper housing 2010, the rotary housing 2050 does not move upwardly along with the delivery tube socket 2040.

In some embodiments, that rotary housing 2050 may further include a limiting structure 2052 for restricting an axial relative position between the delivery tube socket 2040 and the rotary housing 2050.

By providing the axial slide groove 2051, the positioning guide portion 1200 and the limiting structure 2052, the delivery tube socket 2040 may be fixed relative to the rotary housing 2050.

In some embodiments, the limiting structure 2052 may be an elastic snap member. With reference to FIG. 9, one end of the limiting structure 2052 (the elastic snap member) extends radially inward from the rotary housing 2050, and the elastic snap member is configured to: after the delivery tube socket 2040 snaps into a mounting position of the rotary housing 2050 in a first axial direction Y, restrict the delivery tube socket 2040 from moving in a second axial direction opposite to the first axial direction Y. In this way, while facilitating the mounting of the delivery tube socket 2040, the delivery tube socket 2040 is also properly restricted.

In the example shown in FIG. 9, when the delivery tube socket 2040 is assembled into the rotary housing 2050 in the first axial direction Y, the delivery tube socket 2040 may move up and down above the limiting structure 2052 so as to complete a loading action during spraying. However, the limiting structure 2052 can prevent the delivery tube socket 2040 from moving downwardly, thus avoiding undesired slippage of the delivery tube socket 2040.

Although the detailed description makes reference to specific embodiments, the invention shall be defined solely by the appended claims and the equivalents thereof.

What is claimed is:

1. A loading assembly for an inhaler, the loading assembly comprising:
    an actuator;
    a first component comprising a first helical end surface; and
    a second component comprising:
    a helical section having a second helical end surface for mating with the first helical end surface; and
    a horizontal section adjacent to the helical section,
    wherein the first component and the second component are configured such that the second component is capable of moving away from the first component to a preloaded position in the case where the second component rotates relative to the first component in a first direction along the mating first and second helical end surfaces, and
    wherein the actuator is configured to carry the horizontal section to block the second component from leaving the preloaded position in the case where the second component has been moved to the preloaded position,
    wherein the actuator comprises a limiting protrusion for blocking the second component in the preloaded position from rotating in the first direction, and
    wherein the helical section comprises a first sub-section and a second sub-section between the first sub-section and the horizontal section, a recess for accommodating the limiting protrusion of the actuator being provided in the second sub-section.

2. The loading assembly according to claim 1, wherein the recess in the second sub-section is recessed downwardly from the second helical end surface of the second sub-section.

3. The loading assembly according to claim 1, wherein the second helical end surface of the second sub-section is in the same helical surface as the second helical end surface of the first sub-section.

4. The loading assembly according to claim 1, wherein the actuator is partially arranged around at least one of the first component or the second component, and the actuator comprises a bearing surface for carrying the horizontal section, wherein the limiting protrusion is arranged on a radial inner side of the bearing surface, and
    wherein the recess in the second sub-section is arranged on a radial outer side of the second component.

5. The loading assembly according to claim 4, wherein the actuator is configured in the shape of a curved arm arranged around at least one of the first component or the second component, and wherein the curved arm is configured such that when the bearing surface of the curved arm is in contact with the horizontal section of the second component, the limiting protrusion of the curved arm enters the recess in the second sub-section.

6. The loading assembly according to claim 1, wherein the horizontal section has a horizontal end surface, and the second helical end surface of the second sub-section is in a smooth transition with the horizontal end surface.

7. The loading assembly according to claim 1, wherein a bottom surface of the recess of the second sub-section is in a smooth transition with the second helical end surface of the first sub-section.

8. The loading assembly according to claim 1, wherein the recess of the second sub-section makes the second helical end surface of the second sub-section discontinuous from the second helical end surface of the first sub-section.

9. The loading assembly according to claim 1, wherein the second component comprises a second mating portion, the helical section and the horizontal section are arranged on the second mating portion, and the horizontal section has a horizontal end surface; and in the second mating portion, the horizontal end surface is furthest away from a body of the second component, and a distance of the second helical end surface of the helical section from the body of the second component gradually decreases as the helical section extends away from the horizontal section.

10. The loading assembly according to claim 1, wherein the second component further comprises a reinforced section, the reinforced section extending from a body of the second component and being connected to the helical section.

11. The loading assembly according to claim 10, wherein the reinforced section has a third helical end surface, and a step is provided between the third helical end surface and the second helical end surface of the helical section such that the first helical end surface is not in contact with the third helical end surface in the case where the first helical end surface mates with the second helical end surface.

12. The loading assembly according to claim 1, wherein the loading assembly further comprises an elastic member configured to store energy when the second component moves away from the first component, and
    wherein the actuator is configured to, upon being triggered, release the second component such that the second component moves toward the first component to a triggered position under the action of the elastic member.

13. The loading assembly according to claim 1, wherein at least one positioning guide portion is provided at a circumferential edge of the second component.

14. An inhaler, comprising:
    a liquid reservoir; and
    a loading assembly configured to load liquid from the liquid reservoir into a pumping chamber of the inhaler, the loading assembly comprising:
    an actuator;
    a first component comprising a first helical end surface; and
    a second component comprising:
    a helical section having a second helical end surface for mating with the first helical end surface; and
    a horizontal section adjacent to the helical section,
    wherein the first component and the second component are configured such that the second component is capable of moving away from the first component to a preloaded position in the case where the second component rotates relative to the first component in a first direction along the mating first and second helical end surfaces, and
    wherein the actuator is configured to carry the horizontal section to block the second component from leaving the preloaded position in the case where the second component has been moved to the preloaded position, wherein the actuator comprises a limiting protrusion for blocking the second component in the preloaded position from rotating in the first direction, and wherein the helical section comprises a first sub-section and a second sub-section between the first sub-section and the horizontal section, a recess for accommodating the limiting protrusion of the actuator being provided in the second sub-section.

15. The inhaler according to claim 14, wherein the first component is configured as an upper housing of the inhaler and the second component is configured as a delivery tube socket of the inhaler.

16. The inhaler according to claim 15, wherein the inhaler further comprises a rotary housing sleeved outside the delivery tube socket, an inner wall of the rotary housing being provided with an axial slide groove, and wherein a positioning guide portion capable of sliding in the axial slide groove is provided at a circumferential edge of the delivery tube socket, and the positioning guide portion slides into the axial slide groove to restrict relative rotation between the delivery tube socket and the rotary housing.

17. The inhaler according to claim 16, wherein the rotary housing further comprises a limiting structure for limiting an axial relative position between the delivery tube socket and the rotary housing.

18. The inhaler according to claim 17, wherein the limiting structure comprises an elastic snap member, one end of the elastic snap member extending radially inward from the rotary housing, and the clastic snap member being configured to: after the delivery tube socket snaps into a mounting position of the rotary housing in a first axial direction, restrict the delivery tube socket from moving in a second axial direction opposite to the first axial direction.

* * * * *